United States Patent [19]

Viegas et al.

[11] Patent Number: 5,346,703
[45] Date of Patent: * Sep. 13, 1994

[54] BODY CAVITY DRUG DELIVERY WITH THERMO-IRREVERSIBLE POLYOXYALKYLENE AND IONIC POLYSACCHARIDE GELS

[75] Inventors: Tacey X. Viegas, Canton; Lorraine E. Reeve, Dexter; Raymond L. Henry, Grosse Pointe Woods, all of Mich.

[73] Assignee: Mediventures, Inc., Dearborn, Mich.

[ * ] Notice: The portion of the term of this patent subsequent to Dec. 10, 2008 has been disclaimed.

[21] Appl. No.: 939,475

[22] Filed: Aug. 31, 1992

Related U.S. Application Data

[63] Continuation-in-part of Ser. No. 563,640, Aug. 7, 1990, Pat. No. 5,143,731.

[51] Int. Cl.[5] ............... A61K 9/107; A61K 47/34; A61K 47/36
[52] U.S. Cl. .................. 424/486; 424/488; 424/430; 424/434; 424/435; 424/436; 424/437; 514/772.7; 514/779; 514/944; 514/966; 514/967; 252/315.2; 252/315.3; 252/315.4; 523/122
[58] Field of Search ............ 424/486, 488; 514/944; 252/315.3

[56] References Cited

U.S. PATENT DOCUMENTS

| | | | |
|---|---|---|---|
| 2,674,619 | 4/1954 | Lundsted | 260/480 |
| 2,677,700 | 5/1954 | Jackson et al. | 260/488 |
| 2,979,528 | 4/1961 | Lundsted | 260/584 |
| 3,036,118 | 5/1962 | Jackson et al. | 260/484 |
| 3,535,307 | 10/1970 | Moss | 260/209 |
| 3,639,575 | 2/1972 | Schmolka | 424/78 |
| 3,740,421 | 6/1973 | Schmolka | 424/65 |
| 3,829,506 | 8/1974 | Schmolka et al. | 260/260 |
| 3,867,533 | 2/1975 | Schmolka | 424/258 |
| 4,439,196 | 3/1984 | Higuchi | 604/890 |
| 4,465,663 | 8/1984 | Schmolka | 424/62 |
| 4,478,822 | 10/1984 | Haslam | 424/78 |
| 4,495,168 | 1/1985 | Schmolka | 424/45 |
| 4,511,563 | 4/1985 | Schmolka | 514/162 |
| 4,767,619 | 8/1988 | Murray | 424/78 |
| 4,795,642 | 1/1989 | Cohen et al. | 424/455 |
| 4,861,760 | 8/1989 | Mazuel et al. | 514/54 |
| 4,883,660 | 11/1989 | Blackman et al. | 424/78 |
| 4,895,724 | 1/1990 | Cardinal et al. | 424/418 |
| 4,911,926 | 3/1990 | Henry et al. | 424/426 |
| 5,071,644 | 12/1991 | Viegas et al. | 514/772 |
| 5,077,033 | 12/1991 | Viegas et al. | 514/668 |
| 5,124,151 | 6/1992 | Viegas et al. | 424/422 |
| 5,126,141 | 6/1992 | Henry | 424/426 |
| 5,135,751 | 8/1992 | Henry et al. | 424/426 |
| 5,143,731 | 9/1992 | Viegas | 424/486 |

OTHER PUBLICATIONS

Schmolka, I. R., "Artificial Skin I Preparation and Properties of PLURONIC® F-127 Gels for Treatment of Burns", *Journal of Biodmedical Material Research*, vol. 6, p. 571 (1972).

*Primary Examiner*—Edward Webman
*Attorney, Agent, or Firm*—Dykema Gossett

[57] ABSTRACT

Balanced pH, thermo-irreversible gels are ideal vehicles for drug delivery to a body cavity of a mammal. The gels contain a mixture of a polyoxyalkylene block copolymer or polyether together with an ionic polysaccharide which is thermo-irreversibly gelled in the presence of a counter-ion.

28 Claims, 1 Drawing Sheet

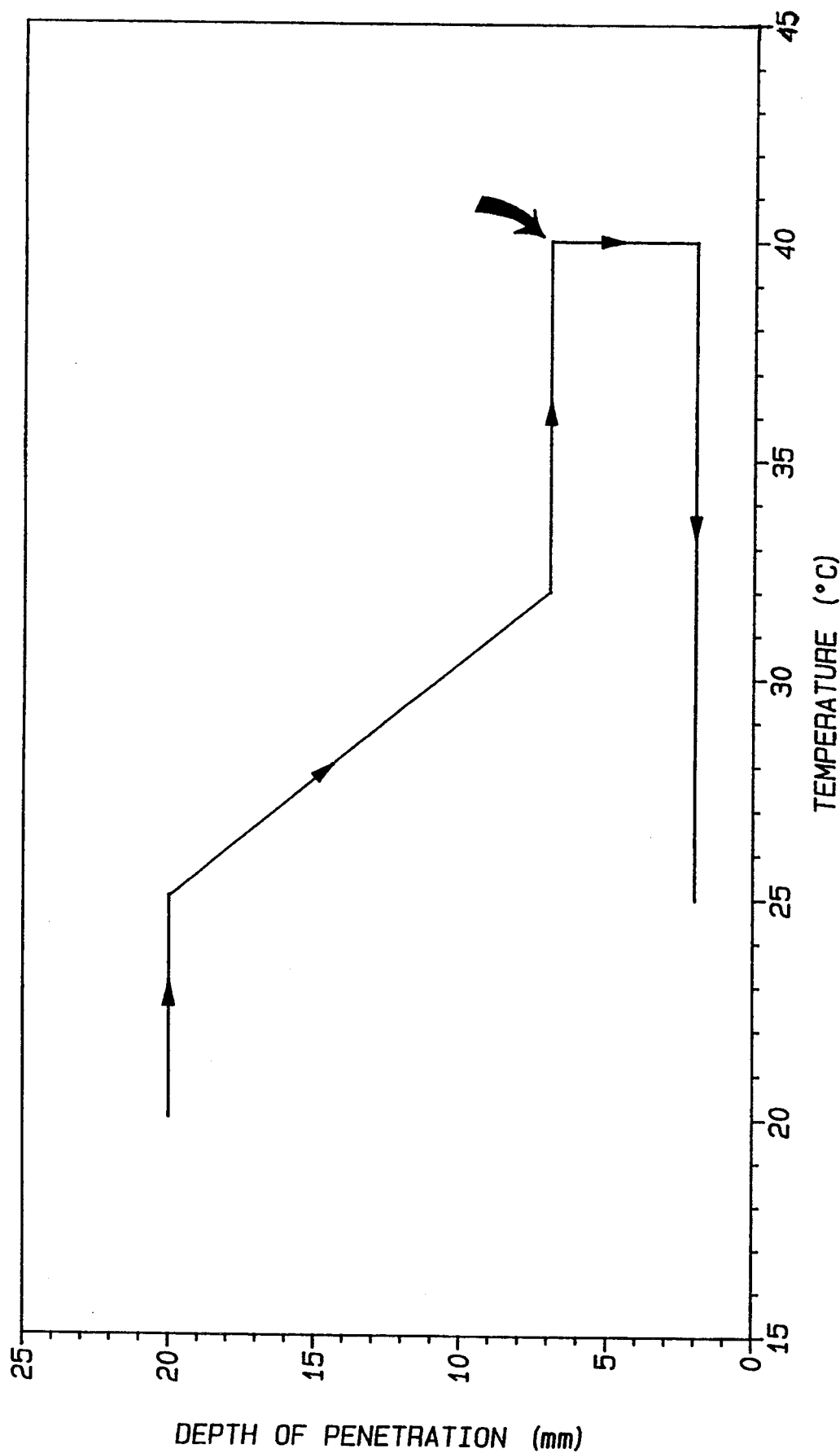

BODY CAVITY DRUG DELIVERY WITH THERMO-IRREVERSIBLE POLYOXYALKYLENE AND IONIC POLYSACCHARIDE GELS

This application is a continuation-in-part of copending application Ser. No. 07/563,640 filed Aug. 7, 1990 now U.S. Pat. No. 5,143,731.

FIELD OF THE INVENTION

This invention relates to body cavity drug delivery systems and pharmaceutical compositions comprising an aqueous gel.

DESCRIPTION OF THE PRIOR ART

Over the years, methods have been developed to achieve the efficient delivery of a therapeutic drug to a mammalian body part requiring pharmaceutical treatment. Use of an aqueous liquid which can be applied at room temperature as a liquid but which forms a semi-solid gel when warmed to body temperature has been utilized as a vehicle for drug delivery since such a system combines ease of application with greater retention at the site requiring treatment than would be the case if the aqueous composition were not converted to a gel as it is warmed to mammalian body temperature. In U.S. Pat. No. 4,188,373, PLURONIC ® polyols are used in aqueous compositions to provide thermally gelling aqueous systems. Adjusting the concentration of the polymer provides the desired sol-gel transition temperature, that is, the lower the concentration of polymer, the higher the sol-gel transition temperature, after crossing a critical concentration below which a gel will not form.

In U.S. Pat. Nos. 4,474,751, 4,474,752, 4,474,753, and 4,478,822, drug delivery systems are described which utilize thermosetting gels; the unique feature of these systems is that both the gel transition temperature and/or the rigidity of the gel can be modified by adjustment of the pH and/or the ionic strength, as well as by the concentration of the polymer.

Other patents disclosing pharmaceutical compositions which rely upon an aqueous gel composition as a vehicle for the application of the drug are U.S. Pat. Nos. 4,883,660, 4,767,619, 4,511,563, and 4,861,760. Thermosetting gel systems are also disclosed for application to injured mammalian tissues of the thoracic or peritoneal cavities in U.S. Pat. No. 4,911,926.

Ionic polysaccharides have been used in the application of drugs by controlled release. Such ionic polysaccharides as chitosan or sodium alginate are disclosed as useful in providing spherical agglomerates of water-insoluble drugs in the *Journal of Pharmaceutical Sciences* volume 78, number 11, November 1989, Bodmeier et al. Alginates have also been used as a depot substance in active immunization, as disclosed in the *Journal of Pathology and Bacteriology* volume 77, (1959), C. R. Amies. Calcium alginate gel formulations have also found use as a matrix material for the controlled release of herbicides, as disclosed in the *Journal of Controlled Release*, 3 (1986) pages 229–233, Pfister et al.

In U.S. Pat. No. 3,640,741, a molded plastic mass composed of the reaction product of a hydrophilic colloid and a cross-linking agent such as a liquid polyol, also containing an organic liquid medium such as glycerin, is disclosed as useful in the controlled release of medication or other additives. The hydrophilic colloid can be carboxymethyl cellulose gum or a natural alginate gum which is cross-linked with a polyol. The cross-linking reaction is accelerated in the presence of aluminum and calcium salts.

In U.S. Pat. No. 4,895,724, compositions are disclosed for the controlled release of pharmacological macromolecular compounds contained in a matrix of chitosan. Chitosan can be cross-linked utilizing aldehydes, epichlorohydrin, benzoquinone, etc.

In U.S. Pat. No. 4,795,642, there are disclosed gelatin-encapsulated, controlled-release compositions for release of pharmaceutical compositions, wherein the gelatin encloses a solid matrix formed by the cation-assisted gelation of a liquid filling composition incorporating a vegetable gum together with a pharmaceutically-active compound. The vegetable gums are disclosed as polysaccharide gums such as alginates which can be gelled utilizing a cationic gelling agent such as an alkaline earth metal cation.

While the prior art is silent with respect to aqueous drug delivery vehicles and isotonicity thereof, osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are enclosed by semipermeable membranes so as to allow the fluids within the chambers to diffuse into the environment into which the osmotic drug delivery system is in contact. The drug delivery device can be sized for oral ingestion, implantation, rectal, vaginal, or ocular insertion for delivery of a drug or other beneficial substance. Since this drug delivery device relies on the permeability of the semipermeable membranes to control the rate of delivery of the drug, the drugs or other pharmaceutical preparations, by definition, are not isotonic with mammalian blood.

SUMMARY OF THE INVENTION

Compositions and a process are disclosed for pharmaceutical compositions containing pharmacologically active medicaments useful in providing treatments to various body cavities of the mammalian body requiring pharmacological treatment. The pharmaceutical compositions of the invention provide a physiologically acceptable medium having a buffered pH and an osmotically balanced vehicle so as to, preferably, provide an isotonic mixture which is iso-osmotic with body fluids and has a similar pH to body fluids, such as blood plasma, lacrimal tears, and the extracellular fluid of exposed tissue, such as is found in the area of third degree burn tissue. The pH and osmotic pressure of such bodily fluids are about pH 7.4 and 290 mosm/kg, respectively. In addition, the pharmaceutical compositions are, optionally, sterilized.

The compositions of the invention in one embodiment comprise aqueous mixtures of a polyoxyalkylene polymer, an ionic polysaccharide, and, optionally, a latent counter-ion useful to gel the polysaccharide upon release of the counter-ion. The counter-ion can be microencapsulated in a heat sensitive medium, for instance, the walls of the microcapsule can be made of mono-, di-, or triglycerides or other natural or synthetic heat sensitive polymer medium. Alternatively, ion exchange resins can be incorporated in the compositions of the invention so as to release the desired counter-ion upon contact with an environment opposite in pH to the pH of the ion exchange resin. The aqueous mixture can be delivered to the body cavities of a mammal requiring treatment as a low viscosity liquid at ambient temperatures which, upon contact with the mammalian body, forms a semisolid gel having a very high viscosity. Alternatively, the counter-ion, instead of being present in a latent form, can be separately applied in an aqueous solution, for instance, by aerosol or non-aerosol spray application to the semisolid gel formed by the polyoxyalkylene polymer upon contact with the mammalian body. Because the preferred pharmaceutical compositions of the invention are low viscosity liquids at ambient temperatures, they insure maximum contact between exposed tissue and the pharmaceutical composition of the invention. The pharmaceutical gel compositions of the invention can be either peeled away or allowed to be absorbed over time. The gels are gradually weakened upon exposure to mammalian body conditions.

Polyphase systems are also useful and may contain non-aqueous solutes, non-aqueous solvents, and other non-aqueous additives. Homogeneous, polyphase systems can contain such additives as water insoluble high molecular weight fatty acids and alcohols, fixed oils, volatile oils and waxes, mono-, di-, and triglycerides, and synthetic, water insoluble polymers without altering the functionality of the system.

A wide variety of polyoxyalkylene polymers are suitable for the preparation of the pharmaceutical compositions of the invention. Generally, it is necessary to adjust the polymer concentration in aqueous solution so as to obtain the desired sol-gel transition temperature in order that the compositions can be provided as low viscosity liquids at ambient temperature, yet form semisolid gels at mammalian body temperatures. In addition to the concentration of the copolymer and the concentration of a water soluble or dispersible pharmacologically active medicament, other suitable excipients must be added so as to provide the desired isotonic, iso-osmotic properties.

The useful polymers which provide the sol-gel characteristics of the pharmaceutical compositions of the invention are, preferably, polyoxyalkylene block copolymers.

The ionic polysaccharides are natural polymers such as chitosan or alginates. Aqueous solutions of these ionic polysaccharides form gels upon contact with aqueous solutions of counter-ions such as calcium, strontium, aluminum, etc., or an aqueous solution of a metal tripolyphosphate.

DESCRIPTION OF THE DRAWING

The drawing provides a curve showing the penetration, as measured by a Precision Universal Penetrometer, of a 20 mm thickness aqueous gel formed by combining Poloxamer 407 with sodium alginate and prepared in accordance with the procedure of Example 1. The scale at the left side of the plot indicates the penetration while the scale on the bottom of the plot indicates the temperature of the composition when tested. The arrow in the plot indicates the point at which an aqueous solution of calcium ions at a concentration of 0,137 molar is made to contact the gelled Poloxamer 407 solution so as to gel the polysaccharide component of the mixture.

DETAILED DESCRIPTION OF THE INVENTION

It has been found that aqueous pharmaceutical vehicles containing a polyoxyalkylene block copolymer, which have the unique feature, in a preferred embodiment, of being liquid at ambient temperatures and transitioning at mammalian body temperatures to a semisolid gel, can be made resistant to shear thinning and the polyoxyalkylene gel made more resistant to penetration by the inclusion of a polysaccharide in admixture with the polyoxyalkylene polymer and contacting the polysaccharide with a counter-ion to gel the polysaccharide. The compositions can be made isotonic, or iso-osmotic, and adjusted to the pH of mammalian body fluids, such as blood plasma, lacrimal tears, and extracellular fluid, such as found in the area of third degree burns. The pH and osmotic pressure of such bodily fluids are generally about 7.4±0.2 and 290±20 mOsm/kg, respectively. It is advantageous to deliver a pharmacologically active medicament to an area of the mammalian body requiring pharmacological treatment under pH and osmotic pressure conditions which match those of bodily fluids. Optionally, the pharmaceutical compositions of the invention can be provided in a sterile condition. The pharmaceutical compositions of the invention can be utilized within bodily cavities such as the rectal, urethral, nasal, vaginal, otic, peritoneal, pleural, oral cavities, or cavities created by injury.

The block copolymer compositions of the invention comprise: at least one polyoxyalkylene block copolymer of the formula

$$Y[(A)_n \text{---} E \text{---} H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyalkylene moiety constituting at least about 60% by weight of the copolymer, as determined by the hydroxyl number of a hydrophobe base intermediate

$$Y[(A)_n \text{---} H]_x \qquad (II)$$

and the total average molecular weight of the copolymer is at least about 5000.

Generally, the polyoxybutylene-based block copolymers useful in the compositions of the invention are prepared by first condensing 1,2-butylene oxide with a water soluble organic compound initiator containing 1 to about 6 carbon atoms, such as 1,4-butylene glycol or propylene glycol, and at least 2 reactive hydrogen atoms to prepare a polyoxyalkylene polymer hydrophobe of at least about 500, preferably, at least about 1,000, and most preferably, at least about 1500 average molecular weight. Subsequently, the hydrophobe is capped with an ethylene oxide residue. Specific methods for preparing these compounds are described in U.S. Pat. No. 2,828,345 and British Patent No. 722,746, both of which are hereby incorporated by reference.

Useful polyoxyethylene-polyoxybutylene based block copolymers conform to the following generic formula:

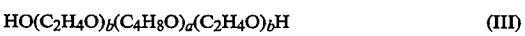
$$HO(C_2H_4O)_b(C_4H_8O)_a(C_2H_4O)_bH \qquad (III)$$

wherein a and b are integers such that the hydrophobe base represented by $(C_4H_8O)_a$ has a molecular weight of at least about 500, preferably, at least about 1000, and most preferably, at least about 3000, as determined by hydroxyl number, the polyoxyethylene chain constituting at least about 60%, preferably, at least about 70% by weight of the copolymer and the copolymer having a total average molecular weight of at least about 5000, preferably, at least about 10,000, and most preferably, at least about 15,000.

The copolymer is characterized in that all the hydrophobic oxybutylene groups are present in chains bonded to an organic radical at the former site of a reactive hydrogen atom thereby constituting a polyoxybutylene base copolymer. The hydrophilic oxyethylene groups are used to cap the polyoxybutylene base copolymer.

Polyoxyethylene-polyoxypropylene block copolymers which can be used to form aqueous gels can be represented by the following formula:

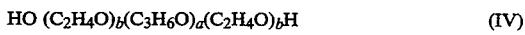

$$HO\,(C_2H_4O)_b(C_3H_6O)_a(C_2H_4O)_bH \quad (IV)$$

wherein a and b are integers such that the hydrophobe base represented by $(C_3H_6O)_a$ has a molecular weight of at least about 900, preferably, at least about 2500, and most preferably, at least about 4000 average molecular weight, as determined by hydroxyl number; the polyoxyethylene chain constituting at least about 60%, preferably, at least about 70% by weight of the copolymer and the copolymer having a total average molecular weight of at least about 5000, preferably, at least about 10,000, and most preferably, at least about 15,000.

Polyoxyethylene-polyoxypropylene block copolymer adducts of ethylenediamine which can be used may be represented by the following formula:

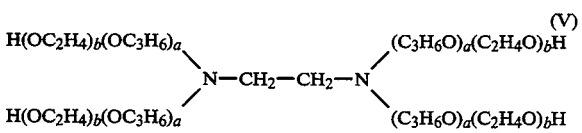

$$\begin{array}{c}H(OC_2H_4)_b(OC_3H_6)_a\\ \diagdown\\ N-CH_2-CH_2-N\\ \diagup\\ H(OC_2H_4)_b(OC_3H_6)_a\end{array}\begin{array}{c}(C_3H_6O)_a(C_2H_4O)_bH\\ \diagup\\ \\ \diagdown\\ (C_3H_6O)_a(C_2H_4O)_bH\end{array} \quad (V)$$

wherein a and b are integers such that the copolymer may have (1) a hydrophobe base molecular weight of at least about 2000, preferably, at least about 3000, and most preferably, at least about 4500, (2) a hydrophile content of at least about 60%, preferably, at least about 70% by weight, and (3) a total average molecular weight of at least about 5000, preferably, at least about 10,000, and most preferably, at least about 15,000.

The hydrophobe base of the copolymer of formula V is prepared by adding propylene oxide for reaction at the site of the four reactive hydrogen atoms on the amine groups of ethylene diamine. An ethylene oxide residue is used to cap the hydrophobe base. The hydrophile polyoxyethylene groups are controlled so as to constitute at least about 60%, preferably, at least about 70% by weight, and most preferably, at least about 80% by weight of the copolymer.

The procedure used to prepare aqueous solutions which form gels of the polyoxyalkylene block copolymers is well known. Either a hot or cold process for forming the solutions can be used. A cold technique involves the steps of dissolving the polyoxyalkylene block copolymer at a temperature of about 5° C. to about 10° C. in water. When solution is complete the system is brought to room temperature whereupon it forms a gel. If the hot process of forming the gel is used, the polymer is added to water heated to a temperature of about 75° C. to about 85° C. with slow stirring until a clear homogenous solution is obtained. Upon cooling, a clear gel is formed. Block copolymer gels containing polyoxybutylene hydrophobes must be prepared by the above hot process, since these will not liquify at low temperatures.

As used herein, the term "gel" is defined as a solid or semisolid colloid containing a certain quantity of water. The colloidal solution with water is often called a "hydrosol".

The organic compound initiator which is utilized in the process for the preparation of the polyoxyalkylene block copolymers generally is water or an organic compound and can contain a plurality of reactive hydrogen atoms. Preferably, Y in formulas I and II above is defined as derived from a water soluble organic compound having 1 to about 6 carbon atoms and containing x reactive hydrogen atoms where x has a value generally, of at least 1, preferably, a value of at least 2. Falling within the scope of the compounds from which Y is derived from water soluble organic compounds having at least two reactive hydrogen atoms are water soluble organic compounds such as propylene glycol, glycerin, pentaerythritol, trimethylolpropane, ethylene diamine, and mixtures thereof and the like.

The oxypropylene chains can optionally contain small amounts of at least one of oxyethylene or oxybutylene groups. Oxyethylene chains can optionally contain small amounts of at least one of oxypropylene or oxybutylene groups. Oxybutylene chains can optionally contain small amounts of at least one of oxyethylene or oxypropylene groups. The physical form of the polyoxyalkylene block copolymers can be a viscous liquid, a paste, or a solid granular material depending upon the molecular weight of the polymer. Useful polyoxyalkylene block copolymers generally have a total average molecular weight of about 5,000 to about 50,000, preferably, about 5,000 to about 35,000 and most preferably, about 10,000 to about 25,000.

In addition to those polyoxyalkylene polymers described above, which are suitable in the formation of the pharmaceutical compositions of the invention, other polyoxyalkylene polymers which form gels at low concentrations in water are suitable. One such polymer is described in U.S. Pat. No. 4,810,503, incorporated herein by reference. These polymers are prepared by capping conventional polyoxyalkylene polyether polyols with an alpha-olefin epoxide having an average of about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactant, which generally do not exceed 10% by weight total. Detailed methods of preparing these aqueous gels are disclosed in U.S. Pat. No. 4,810,503. Preparation of said aqueous gels is generally described below. Preferred surfactants for use in preparing these gels are also disclosed in said patent.

A conventional copolymer polyether polyol is prepared by preparing block or heteric intermediate polymers of ethylene oxide and at least one lower alkylene oxide having 3 to 4 carbon atoms as intermediates. These are then capped with the alpha-olefin epoxide to prepare the polymers. Ethylene oxide homopolymers capped with said alpha-olefin oxides are also useful as intermediates.

The heteric copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C. to 150° C., preferably from 80° C. to 130° C., under an inert gas pressure preferably from about 30 psig to 90 psig.

A block copolymer intermediate is prepared by reacting either the ethylene oxide or said alkylene oxide having 3 to 4 carbon atoms with said active hydrogen-containing compound followed by reaction with the other alkylene oxide.

The ethylene oxide and the alkylene oxides having from 3 to 4 carbon atoms are used in said intermediates in amounts so that the resulting polyether product will contain at least 10 percent by weight, preferably about 70 percent to about 90 percent by weight, ethylene oxide residue. The ethylene oxide homopolymer intermediate is prepared by reacting ethylene oxide with said active hydrogen-containing compound. The reaction conditions for preparing the block copolymer and ethylene oxide homopolymer intermediates are similar to those for the heteric copolymer intermediate. The temperature and pressure are maintained in the above ranges for a period of about one hour to ten hours, preferably one to three hours. A suitable molecular weight of the polyether copolymer is between about 10,000 to about 100,000.

The alpha-olefin oxides which are utilized to modify the conventional polyether intermediate of the prior art are those oxides and the commercially available mixtures thereof generally containing an average of about 20 to 45, preferably about 20 to 30, carbon atoms. The amount of alpha-olefin required to obtain the more efficient capped polyethers is generally about 0.3 to 10 percent, preferably about 4 to 8 percent, of the total weight of the polyethers.

Since the preparation of heteric and block copolymers of alkylene oxides and ethylene oxide homopolymers is well known in the art, further description of the preparation of said copolymers is unnecessary. Further details of the preparation of heteric copolymers of lower alkylene oxide can be obtained in U.S. Pat. No. 3,829,506, incorporated herein by reference. Further information on the preparation of block copolymers of lower alkylene oxides can be obtained in U.S. Pat. Nos. 3,535,307, 3,036,118, 2,979,578, 2,677,700, and 2,675,619 incorporated herein by reference.

The surfactants may be ionic or nonionic and many surfactants and types of surfactants may be employed. While all surfactants may not be effective in the preparation of the isotonic gels of the instant invention, the fact that many are effective makes it a simple matter for one skilled in the art to select such surfactant with a minimum of trial and error.

The amounts of capped polyether polymer and surfactant may be as little as 1.0 percent by weight or less of each depending on the type and amount of the other component. There appears to be no maximum amount of either component than that dictated by economic considerations. However, the total amount of capped polymer and surfactant would generally not exceed 10 percent by weight.

The ionic polysaccharides found useful in the present invention are hydrophilic colloidal materials and include the natural gums such as alginate gums, i.e., the ammonium and alkali metal salts of alginic acid and mixtures thereof as well as chitosan, which is a common name for the deacetylated form of chitin. Chitin is a natural product comprising poly (N-acetyl-D-glucosamine). The alginates are available as dry powders from Protan, Inc., Commack, N.Y. and from Kelco Company, San Diego, Calif.

The alginates can be any of the water-soluble alginates including the alkaline metal (sodium, potassium, lithium, rubidium and cesium) salts of alginic acid, as well as the ammonium salt, and the soluble alginates of an organic base such as mono-, di-, or triethanolamine, aniline, and the like.

Useful counter-ions for gelling the alginate ionic polysaccharide in combination with the polyoxyalkylene copolymers compositions of the invention are cationic gelling agents preferably, comprising a divalent or trivalent cation. Useful divalent cations include the alkaline earth metals, preferably, selected from the group consisting of calcium and strontium. Useful trivalent cations include aluminum, chromium, and iron. The preferred counter-ions for gelling the alginate ionic polysaccharide are contained in ionic compounds selected from pharmaceutically-acceptable gluconates, fluorides, citrates, phosphates, tartrates, sulfates, acetates, borates, chlorides, and the like having alkaline earth metal cations such as calcium and strontium. Especially preferred counter-ion containing inorganic salts for use as ionic polysaccharide gelling agents include such inorganic salts as the chloride salts, such as strontium chloride, calcium chloride, and mixtures thereof.

While the counter-ion such as calcium or other counter-ions may be obtained by contact with bodily fluids, it is preferred that the counter-ion in latent form be added to the ionic polysaccharide and polyoxyalkylene copolymer compositions of the invention. Alternatively, a counter-ion can be added to the ionic polysaccharide and polyoxyalkylene copolymer compositions of the invention utilizing a two part system in which the counter-ion is topically applied to the remaining components of the drug delivery system subsequent to their topical application to a body cavity. It is preferred to incorporate the counter-ion in a latent form together with the ionic polysaccharide and polyoxyalkylene copolymer compositions of the invention. This may be accomplished by either encapsulating an aqueous solution of one of the counter-ion gelling agents, previously described above, or by the incorporation of the counter-ion gelling agent into a matrix which provides for the controlled, slow-release of the gelling agent. For instance, the counter-ion can be incorporated into an ion exchange resin or gelatin-encapsulated controlled-release compositions can be used, as disclosed in U.S. Pat. No. 4,795,642, incorporated herein by reference. In this patent there is disclosed the preparation of a gelatin shell encapsulating a controlled-release formulation in which the gelatin composition includes calcium chloride as a gelling agent. Alternatively, the counter-ion can be incorporated as an aqueous solution of a counter-ion gelling agent encapsulated in a vesicle composed, for instance, of alpha-tocopherol, as disclosed in U.S. Pat. No. 4,861,580.

Generally, aqueous solutions of chitosan can be gelled with multivalent anion gelling agents, preferably, comprising a metal polyphosphate, such as an alkali metal or ammonium polyphosphates, pyrophosphates, sodium and potassium metaphosphates, and sodium and ammonium (mono-, di-, tri-) phosphates. Generally, a molar ratio of counter-ion to chitosan or alginate of about 1:1 to about 10:1, preferably, about 2:1 to about 5:1, and, most preferably, about 3:1 to about 5:1 is used to render the compositions of the invention thermally-irreversibly gelled.

With specific reference to the application of the pharmaceutical drug delivery compositions of the invention to a body cavity, such as the rectum, urethra, nasal cavity, vagina, auditory meatus, oral cavity, buccal pouch, peritoneum, or pleura, each of these areas desirably require, for the avoidance of adverse physiological effects to the area requiring pharmacological treatment, that the pH and the osmolality of the pharmaceutical vehicle be matched to the pH and osmolality of the bodily fluids present at the area of treatment.

In general, the preferred drug delivery system of the present invention will contain from about 0.01% to about 60% by weight of the medicament or pharmaceutical, from about 10 to about 50% by weight of the polyoxyalkylene copolymer, about 0.2 to about 2.5% by weight, preferably, about 0.5 to about 1.5% by weight of ionic polysaccharide, and from 80% to about 20% water. In special situations, however, the amounts may be varied to increase or decrease the dosage schedule.

If desired, the drug delivery vehicle may also contain preservatives, cosolvents, suspending agents, viscosity enhancing agents, ionic strength and osmolality adjusters and other excipients in addition to the medicament and buffering agents. Suitable water soluble preservatives which may be employed in the drug delivery vehicle are sodium bisulfite, sodium thiosulfate, ascorbate, benzalkonium chloride, chlorobutanol, thimerosal, phenylmercuric borate, parabens, benzyl alcohol, and phenylethanol and others. These agents may be present, generally, in amounts of about 0,001% to about 5% by weight and, preferably, in the amount of about 0.01% to about 2% by weight.

Suitable water soluble buffering agents are alkali or alkali earth carbonates, phosphates, bicarbonates, citrates, borates, acetatee, succinates and the like, such as sodium phosphate, citrate, borate, acetate, bicarbonate, carbonate and trimethamine (TRIS). These agents are present in amounts sufficient to maintain the pH of the system at 7.4±0.2 and, preferably, 7.4. As such the buffering agent can be as much as 5% on a weight basis of the total composition.

The pharmaceutical vehicles for drug delivery of the invention are an improvement over these prior art methods of body cavity drug delivery in that the preferred compositions are not only optimized for physiological tolerance in the body cavity preferably by formulating the drug delivery compositions so as to have isotonic characteristics but are made more resistant to shear thinning as the result of higher gel strength. These advantages are obtained by the incorporation of an ionic polysaccharide in admixture with a polyoxyalkylene copolymer. By matching the osmolality of the drug delivery compositions of the invention to those of the bodily fluids, it is possible to eliminate burning or other discomfort upon application of the drug delivery systems of the invention. The higher gel strength compositions upon contact with a counter-ion for the ionic polysaccharide allow retention of the gel at the desired locus for longer intervals, thus, increasing the efficacy of the delivered drug.

Many pharmaceutically active materials may be delivered to body cavities by the drug delivery system of this invention. Preferably, the drug, or pharmaceutical, is water soluble. Some drugs will show greater solubility in the aqueous copolymer system than others. Cosolvents can be used to enhance drug solubility. However, some drugs may be insoluble. These can often be suspended in the polymer vehicle with the aid of suitable suspending or viscosity-enhancing agents.

Suitable classes of drugs which can be administered to a body cavity by the drug copolymer delivery system of the present invention are antibacterial substances such as β-lactum antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanarnycin, amikacin, sisomicin and tobramycin; nalidixic acids and analogs such as norfloxacin and the antimicrobial combination of fluoroalanine/pentizidone; nitrofurazones, and the like; antihistaminics and decongestants such as pyrilamine, chlospheniramine, tetrahydrazaline, antazoline, and the like; anti-inflammatories such as cortisone, hydrocortisone, beta-methasone, dexamethasone, fluocortolone, prednisolone, triamcinolone, indomethacin, sulindac, its salts and its corresponding sulfide, and the like. Also included are antiparasitic compounds such as ivermectin; antiviral effective compounds such as acyclovir and interferon and spermicidals such as nonoxynal.

For treatment of vaginal and urethral conditions requiring antifungal, amoebicidal, trichomonacidal agents or antiprotozoals, the following agents can be used: polyoxyethylene nonylphenol, alkylaryl sulfonate, oxyquinoline sulfate, miconazole nitrate, sulfanilamide, candicidin, sulfisoxazole, nystatin, clotrimazole, metronidazole and the like and antiprotozoals such as chloramphenicol, chloroquine, trimethoprim, sulfamethoxazole and the like.

For use rectally the following suitable drugs can be administered by the drug copolymer delivery system of the present invention:

(1) Analgesics such as aspirin, acetaminophen, diflunisal and the like;

(2) anesthetics such as lidocaine, procaine, benzocaine, xylocaine and the like;

(3) antiarthritics such as phenylbutazone, indomethacin, sulindac, dexamethasone, ibuprofen, allopurinol, oxyphenbutazone, probenecid and the like;

(4) antiasthma drugs such as theophylline, ephedrine, beclomethasone dipropionate, epinephrine and the like;

(5) urinary tract disinfectives such as sulfamethoxazole, trimethoprim, nitrofurantoin, norfloxacin and the like;

(6) anticoagulants such as heparin, bishydroxycoumarin, warfarin and the like;

(7) anticonvulsants such as diphenylhydantoin, diazepam and the like;

(8) antidepressants such as amitriptyline, chlordiazepoxide, perphenazine, protriptyline, imipramine, doxepin and the like;

(9) antidiabetics such as insulin, tolbutamide, tolazamide, acetohexamide, chlorpropamide and the like;

(10) antineoplastics such as adriamycin, fluorouracil, methotrexate, asparaginase and the like;

(11) antipsychotics such as prochlorperazine, lithium carbonate, lithium citrate, thioridazine, molindone, fluphenazine, trifluoperazine, perphenazine, amitriptyline, triflupromazine and the like;

(12) antihypertensive such as spironolactone, methyldopa, hydralazine, clonidine, chlorothiazide, deserpidine, timolol, propranolol, metoprolol, prazosin hydrochloride, reserpine and the like;

(13) muscle relaxants such as melphalan, dantrolene, cyclobenzaprine, methocarbamol, diazepam and the like; and

(14) antiprotozoals such as chloramphenicol, chloroquine, trimethoprim, sulfamethoxazole, and the like.

Typically as stated previously, the present liquid drug delivery device can contain from about 0.01% to about 60% of the medicament, or pharmaceutical, on a weight to weight basis. Thus, from one gram of the liquid composition containing about 1 ml of solution, one would obtain about 0.1 mg to about 600 mg of drug.

The particular drug used in the pharmaceutical composition of this invention is the type which a patient would require for pharmacological treatment of the condition from which said patient is suffering. For example, if the patient is suffering from pain or itch of the external auditory canal, the drug of choice would probably be benzocaine.

Also included in this invention is the use of the drug delivery device or pharmaceutical composition minus the active drug or medicament for restoration or maintenance of vaginal acidity. All the ratios of components as described above would be satisfactory for this composition. For this use one would administer the vehicle as needed at the desired pH.

Representative buffering agents or salts useful in maintaining the pH at about 7.4±0.2 are alkali or alkali earth carbonates, chlorides, sulfates, phosphates, bicarbonates, citrates, borates, acetates, succinates and tromethamine (TRIS). Representative preservatives are sodium bisulfite, sodium thiosulfate, ascorbate, benzalkonium chloride, chlorobutanol, thimerosal, phenylmercuric borate, parabens, benzyl alcohol and phenylethanol.

The preparation of the pharmaceutical drug delivery compositions of the invention are described below. The Examples which follow were prepared according with the following preparation procedure. Since the polyoxyalkylenes dissolve more completely at reduced temperatures, the preferred methods of solubilization are to add the required amount of copolymer to the amount of water to be used. Generally after wetting the copolymer by shaking, the mixture is capped and placed in a cold chamber or in a thermostatic container at about 0° C. to 10° C. in order to dissolve the copolymer. The mixture can be stirred or shaken to bring about a more rapid solution of the polymer. The pharmacologically active medicaments and various additives such as buffers, salts, and preservatives can subsequently be added and dissolved. In some instances the pharmacologically active substance must be suspended since it is insoluble in water. The pH of 7.4±0.2 is obtained by the addition of appropriate buffering agents.

The following Examples illustrate the various aspects of the invention but are not intended to limit its scope. Where not otherwise specified throughout this specification and claims, temperatures are given in degrees centigrade and parts, percentages, and proportions are by weight.

EXAMPLE 1

This Example formulation describes a composition of the invention characterized as iso-osmotic, sterile, and having a pH of 7.4±0.2. An aqueous solution was made of a polyoxyethylene-polyoxypropylene block copolymer having the structure generically shown above as Formula IV and having a polyoxypropylene hydrophobe base average molecular weight of about 4000, a total average molecular weight of about 11,500, and containing oxyethylene groups in the amount of about 70% by weight of the total weight of copolymer. This copolymer (Formula VI below) is sold under the trademark PLURONIC© F-127 (also known as Poloxamer 407) by the BASF Corporation, Parsippany, N.J. A solution in TRIS hydrochloride buffer was made by dissolving said copolymer and sodium alginate in cold (4° C.) buffer to give a concentration of 19% by weight polyoxyalkylene and 1% by weight sodium alginate. More specific solution procedures are described in "Artificial Skin I Preparation and Properties of PLURONIC F-127 Gels For Treatment of Burns", *Journal of Biomedical Material Research* 6, 527, 1972, incorporated herein by reference. The block copolymer has the formula:

$$\text{H[OCH}_2\text{CH}_2]_{49}[\text{OCHCH}_2]_{67}[\text{OCH}_2\text{CH}_2]_{49}\text{OH} \quad \text{(VI)}$$

with CH$_3$ substituent on the middle block.

This formulation forms the basis for the Figure in which the curve shows the penetration of a 20mm thickness aqueous gel at various temperatures. After contact of the gel with calcium ions, as indicated by the arrow at 40° C., the gel strength is not reduced or the composition rendered fluid by lowering the temperature back to 25° C.

EXAMPLE 2 (Inventive) AND EXAMPLE 3 (Control)

These examples describe hyperosmotic, pH balanced, thermo-sensitive systems, in which the active ingredient is dissolved. The following antibacterial formulations were prepared to contain 11.2% by weight of mafenide acetate. The antibacterial formulations were prepared as follows:

| Ingredient | Percent by Weight | |
|---|---|---|
|  | Example 2 | Example 3 (Control) |
| mafenide acetate | 11.2 | 11.2 |
| sodium alginate | 0.5 | — |
| carrageenan | — | 0.5 |
| Poloxamer 407 (BASF) | 19.0 | 19.0 |
| TRIS hydrochloride buffer (0.1 molar) | 69.3 | 69.3 |

The formulations were prepared by dissolving the drug and sodium alginate or carrageenan by stirring in the required amount of TRIS hydrochloride buffer. These ingredients in a glass beaker were placed in an ice bath and the Poloxamer 407 was added to the beaker slowly while stirring. After the Poloxamer 407 was completely dissolved, the formulation was stored at 4° C. The entire process was carried out under a nitrogen atmosphere. The product obtained was characterized as clear, straw colored and exhibiting gelation at the temperature of mammalian skin (33±2° C.). In the gelled state, the pH and osmolality of the preparation would be expected to be 7.5 and over 720 mOsm/Kg, respectively. Iso-osmotic solutions containing 2.5 to 3% by weight mafinide acetate would be expected to be iso-osmetic in the liquid state but less therapeutically effective.

The solutions of Examples 2 and 3 were exposed to an equal amount of 2% by weight solution of calcium chloride. The solution of Example 2 formed a thermo-irreversible gel. The solution of Example 3 remained thermo-reversible. Comparison of these examples illustrates the importance of utilizing an ionic (sodium alginate) instead of a nonionic polysaccharide (carrageenan). In these examples, the 2% solution of calcium chloride was applied both as a spray to the solution of Examples 2 and 3 and also the 2% solution of calcium chloride was used to impregnate a gauze bandage and subsequently the solutions of Examples 2 and 3 were placed in contact with the gauze bandage. In both cases, the solution of Example 2 was rendered thermo-irreversible and the solution of Example 3 was unaffected.

EXAMPLES 4 (Inventive) AND 5 (Control)

Examples 2 and 3 are repeated substituting for Poloxamer 407, 2% by weight of polymer #2, as described in U.S. Pat. No. 4,810,503 and 4% by weight of surfactant #1, as described therein. The balance of the percentage of Poloxamer 407 used in Examples 2 and 3 is made up with TRIS hydrochloride buffer. These formulations form soft gels at room temperature which are usefully stiffened upon exposure to a 2% by weight aqueous solution of calcium chloride, in the case of Example 4, and are unaffected in the case of control Example 5. Substantially similar pH and osmolality results are obtained.

EXAMPLE 6

Ion exchange resin beads sold under the trade name Duolite were treated so as to incorporate calcium by first treating a 30 gram sample of the ion exchange resin with a solution of 0.1 molar hydrochloric acid so as to allow for the exchange of protons for sodium. After three washings with 0.1 molar hydrochloric acid, the beads were washed with water and then washed twice with a 2% aqueous solution of calcium chloride. Each of the washing steps took place over a period of 16 hours (overnight). The beads were thereafter filtered and washed with water utilizing coarse filter paper and a Buchner glass filter assembly. The beads were then left overnight in a desiccator to dry.

The dried beads of ion exchange resin which were obtained were utilized in the amount of 2 grams to fill a first compartment (close to the needle of the syringe) of a glass syringe utilized to apply liquids and dry materials. The syringe is sold under the trade name Hypak. Into the second compartment of the syringe, there was placed the solution of Example 2. Pushing the plunger of the syringe forward resulted in mixing the solution of Example 2 with the ion exchange beads. After 5 to 10 minutes subsequent to mixing, the mixture was expelled from the syringe. After an additional 15 minutes, the expelled material formed a thermo-irreversible film on the substrate on which it was expelled.

While this invention has been described with reference to certain specific embodiments, it will be recognized by those skilled in the art that many variations are possible without departing from the scope and spirit of the invention, and it will be understood that it is intended to cover all changes and modifications of the invention, disclosed herein for the purpose of illustration, which do not constitute departures from the spirit and scope of the invention.

That which is claimed:

1. A pharmaceutical aqueous gel composition, said composition comprising
   (1) about 0.2% to about 2.5% by weight of an ionic polysaccharide;
   (2) about 10% to about 50% by weight of a polyoxyalkylene block copolymer of general formula $$Y[(A)_n \text{---} E \text{---} H]_x$$

where A is a polyoxyalkylene moiety having an oxygen/carbon atom ratio of less than 0.5, x is at least 2, Y is derived from water or an organic compound containing x reactive hydrogen atoms, E is a polyoxyethylene moiety constituting at least 60 percent by weight of the polyoxyalkylene block copolymer, n has a value such that the minimum molecular weight of A is between about 500 and about 900, as determined by the hydroxyl number of an intermediate of general formula $$Y[(A)_n \text{---} H]_x$$

and the average molecular weight of the polyoxyalkylene block copolymer is between about 5000 and about 50,000;
   (3) about 0.01% to about 60% by weight of a pharmacologically effective amount of a drug selected from the group consisting of antibacterials, antihistamines, decongestants, antiinflammatories, antiparasitics, antivirals, local anesthetics, antifungals, analgesics, antiarthritics, antiastrunatics, anticoagulants, anticonvulsants, antidepressants, antidiabetics, antieoplastics, antpsychotics, antihypertensives, spermicidals, and muscle relaxants;
   (4) a pharmaceutically acceptable buffer sufficient to maintain the $p_H$ of the aqueous gel composition at a desired level; and
   (5) optionally, a latent form of a counter-ion capable of cross-linking the ionic polysaccharide, wherein the aqueous gel composition is a liquid at room temperature or below and a gel at mammalian body temperature.

2. The composition of claim 1, wherein the polyoxyalkylene block copolymer is prepared using a water soluble organic initiator Y having 1 to about 6 carbon atoms and wherein the pH of the aqueous gel composition is maintained at about 7.4 and the osmolality of the aqueous gel composition at mammalian body temperature is about 290 mOsm/kg.

3. The composition of claim 2, wherein the polyoxyalkylene moiety is derived from an alkylene oxide selected from the group consisting of butylene oxide, propylene oxide, and mixtures thereof and Y is derived from an organic compound selected from the group consisting of propylene glycol, glycerin, pentaerythritol, trimethylpropane, ethylenediamine, and mixtures thereof.

4. The composition of claim 3, wherein the polyoxyalkylene block copolymer is a polyoxyethylene-polyoxypropylene block copolymer wherein the polyoxyethylene moiety constitutes at least about 70 percent by weight of the polyoxyalkylene block copolymer, wherein the average molecular weight of A is at least 1200, and wherein the molecular weight of the polyoxyalkylene block copolymer is at least about 5,000.

5. The composition of claim 4, wherein the intermediate is prepared by initiation with propylene glycol and has a molecular weight of at least 1500.

6. The composition of claim 5, wherein the polyoxyalkylene block copolymer has:
   (1) general formula $$HO(C_2H_4O)_b(C_4H_8O)_8(C_2H_4O)_bH$$

wherein a and b are integers such that the hydrophobe base represented by $(C_4H_8O)_a$ has a molecular weight of at least about 500 as determined by hydroxyl number, the polyoxyethylene chain constitutes at least about 70 percent by weight of the polyoxyalkylene block copolymer, and the polyoxyalkylene block copolymer has an average molecular weight of at least 5,000; or (2) general formula $$HO(C_2H_4O)_b(C_3H_6O)_8(C_2H_4O)_bH$$

wherein a and b are integers such that the hydrophobe base represented by $(C_3H_6)_a$ has a molecular weight of at least about 900 as determined by hydroxyl number, the polyoxyethylene chain constitutes at least about 70 percent by weight of the polyoxyalkylene block copolymer, and the polyoxyalkylene block copolymer has an average molecular weight of at least 5,000; or (3) general formula

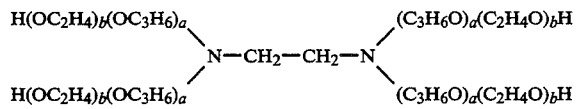

wherein a and b are integers such that the polyoxyalkylene block copolymer has a hydrophobe molecular weight of at least about 1500, a hydrophobe content of at least about 70 percent by weight, and an average molecular weight of at least 5,000.

7. The composition of claim 6, wherein the polyoxyalkylene block copolymer is of average formula

and wherein the polyoxyalkylene block copolymer constitutes about 10 to about 40 percent by weight of the composition.

8. The composition of claim 6, wherein the polyoxyalkylene block copolymer constitutes about 15 to about 30 percent by weight of the composition, the optional latent form of the counter-ion is present as a microencapsulated component or as an ion-exchange resin, the counter-ion is selected from the group consisting of calcium, strontium, and aluminum, and the ionic polysachharide is an ammonium alginate, a metal alginate, or mixtures thereof wherein said counter-ion and said alginate being present at a molar ratio between about 1:1 to about 10:1.

9. The composition of claim 6, wherein the polyoxyalkylene block copolymer constitutes abut 15 to about 30 percent by weight of the composition, the optional latent form of the counter-ion is present es a microencapsulated components or as an ion-exchange resin, the counter-ion is selected from the group consisting of metal phosphates, metaphosphates, pyrophosphates, and tripolyphosphates, and the ionic polysaccharide is chitosan wherein said counter-ion and said chitosan being present at a molar ratio between about 1:1 about 10:1.

10. A hyperosomotic, iso-osmotic, or hypoosmotic aqueous gel composition comprising (1) about 0.2% to about 2.5% by weight of an ionic polysaccharide;

(2) about 10% to about 50% by weight of a polyoxyalkylene block copolymer of general formula $$Y[(A)_n \text{---} E \text{---} H]_x$$

where A is a polyoxyalkylene moiety having an oxygen/carbon atom ratio of less than 0.5, x is at least 2, Y is derived from water or an organic compound containing x reactive hydrogen atoms, E is a polyoxyethylene moiety constituting at least 60 percent by weight of the polyoxyalkylene block copolymer, n has a value such that the minimum molecular weight of A is between about 500 and about 900, as determined by the hydroxyl number of an intermediate of general formula $$Y[(A)_n \text{---} H]_x$$

and the average molecular weight of the polyoxyalkylene block copolymer is between about 5000 and about 50,000; and (3) optionally, a latent form of a counter-ion capable of cross-linking the ionic polysaccharide, wherein the aqueous gel composition is a liquid at room temperature or below and a gel at mammalian body temperature.

11. The composition of claim 10, wherein the polyoxyalkylene block copolymer is prepared using a water soluble organic initiator Y having 1 to about 6 carbon atoms and wherein the pH of the composition is maintained at about 7.4 and the osmolality of the composition at mammalian body temperature is about 290 mOsm/kg.

12. The composition of claim 11, wherein the polyoxyalkylene moiety is derived from an alkylene oxide selected from the group consisting of butylene oxide, propylene oxide, and mixtures thereof and Y is derived from an organic compound selected from the group consisting of propylene glycol, glycerin, pentaerythritol, trimethylpropane, ethylenediamine, and mixtures thereof.

13. The composition of claim 12, wherein the polyoxyalkylene block copolymer is a polyoxyethylene-polyoxypropylene block copolymer wherein the polyoxyethylene moiety constitutes at least about 70 percent by weight, wherein the average molecular weight of A is at least 1200, and wherein the molecular weight of the polyoxyalkylene block copolymer is at least about 5,000.

14. The composition of claim 13, wherein the intermediate is prepared by initiation with propylene glycol and has a molecular weight of at least 1500.

15. The composition of claim 14, wherein the polyoxyalkylene block copolymer has:

(1) general formula $$HO(C_2H_4O)_b(C_4H_8O)_8(C_2H_4O)_bH$$

wherein a and b are integers such that the hydrophobe base represented by $(C_4H_8O)_8$ has a molecular weight of at least about 500 as determined by hydroxyl number, the polyoxyethylene chain constitutes at least about 70 percent by weight of the polyoxyalkylene block copolymer, and the polyoxyalkylene block copolymer has an average molecular weight of at least 5,000; or (2) general formula $$HO(C_2H_4O)_b(C_3H_6O)_8(C_2H_4O)_bH$$

wherein a and b are integers such that the hydrophobe base represented by $(C_3H_6O)_8$ has a molecular weight of at least about 900 as determined by hydroxyl number, the polyoxyethylene chain constitutes at least about 70 percent by weight of the polyoxyalkylene block copolymer, and the polyoxyalkylene block copolymer has an average molecular weight of at least 5,000; or (3) general formula

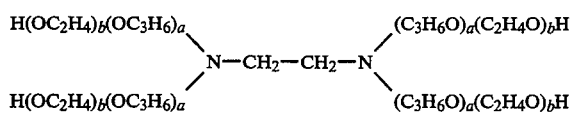

wherein a and b are integers such that the polyoxyalkylene block copolymer has a hydrophobe molecular weight of at least about 1500, a hydrophobe content of at least about 70 percent by weight, and an average molecular weight of at least 5,000.

16. The composition of claim 15, wherein the polyoxyalkylene block copolymer is of average formula

and wherein the polyoxyalkylene block copolymer constitutes about 10 to about 40 percent by weight of the composition.

17. The composition of claim 15, wherein the polyoxyalkylene block copolymer constitutes about 15 to about 30 percent by weight of the composition, the optional latent form of tile counter-ion is present as a microencapsulated component or as an ion-exchange resin, the counter-ion is selected from the group consisting of calcium, strontium, and aluminum, and the ionic polysaccharide is an ammonium alginate, a metal alginate, or mixtures thereof wherein said counter-ion and said alginate being present at a molar ratio between about 1:1 to about 10:1.

18. The composition of claim 15, wherein the polyoxyalkylene block copolymer constitutes about 15 to about 30 percent by weight of the composition, the optional latent form of the counter-ion is present as a microencapsulated component or as an ion-exchange resin, the counter-ion is selected from the group consisting of metal phosphates, pyrophosphates, and tripolyphosphates, and the ionic polysaccharide is chitosan wherein said counter-ion and said chitosan being present at a molar ratio between about 1:1 to about 10:1.

19. A hyperosmottc, iso-osmotic, or hypoosmotic aqueous gel composition having a desired osmolality and pH, said composition comprising
(1) about 0,2% to about 2.5% by weight of an ionic polysaccharide;
(2) about 0.1% to about !0% by weight of a combination of a surfactant and a polyoxyalkylene polyether, wherein sais polyether having a molecular weight of about 10,000 to about 100,000 which is selected from the group consisting of
(A) a polyoxalkylene polyether prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heretic or block copolymer intermediate and further reacting the copolymer intermediate with at least one alpha-olefin oxide having an average carbon chain length of about 20 to about 45 aliphatic carbon atoms, wherein the alpha-olefin oxide is present in the amount of about 0.3 to about 10 percent by weight based on the total weight of the polyether; and
(B) a polyoxalkylene polyether prepared by reacting ethylene oxide with at least one active hydrogen-containing compound having from 2 to 10 carbon atoms and from 2 to 6 active hydrogens to prepare a homopolymer intermediate and further reacting the homopolymer intermediate with at least one alpha-olefin oxide having an average carbon chain length of about 20 to 45 aliphatic carbon atoms, wherein the alpha-olefin oxide is present in the amount of about 0.3 to 10 percent by weight based on the total weight of the polyether; and
(3) optionally, a latent form of a counter-ion capable of cross-linking the ionic polysaccharide.

20. A composition as defined in claim 19, wherein the polyether is polyether (A) and the pH of the composition is maintained at about 7.4 and the osmolality of the composition at mammalian body temperature is about 290 mOsm/kg.

21. A composition as defined in claim 19, wherein the polyether is polyether (B) and the pH of the composition is maintained at about 7.4 and the osmolality of the composition at mammalian body temperature is about 290 mOsm/kg.

22. The composition as defined in claim 19, wherein the optional latent form of the counter-ion is present as a microencapsulated component or as an ion-exchange resin, the counter-ion is selected from the group consisting of calcium, strontium, and aluminum, and the ionic polysaccharide is an ammonium alginate, a metal alginate, or mixtures thereof wherein said counter-ion and said alginate being present at a molar ratio between about 1:1 to about 10:1.

23. The composition as defined in claim 19, wherein the optional latent form of the counter-ion is present as a microencapsulated components or as an ion-exchange resin, the counter-ion is selected from the group consisting of metal phosphates, metaphosphates, pyrophosphates, and tripolyphosphates, and the ionic polysaccharide is chitosan wherein said counter-ion and said chitosan being present at a molar ratio between about 1:1 to about 10:1.

24. A composition as defined in claim 19, wherein said composition further contains:
(1) a pharmacologically effective amount of a drug selected from the group consisting of antibacterials, antihistamines, decongestants, anti-inflammatories, antiparasitics, antivirals, local anesthetics, antifungals, trichomonocidal, analgesics, antiarthritics, antiasthmatics, anticoagulants, anticonvulsants, antidepressants, antidiabetics, antineoplastics, antipsychotics, antihypertensives, spermicidals, and muscle relaxants; and
(2) a pharmaceutically acceptable buffer sufficient to maintain the pH of the aqueous gel composition at the desired level.

25. A composition as defined in claim 24, wherein the polyether is polyether (A) and the pH of the composition is maintained at about 7.4 and the osmolality of the composition at mammalian body temperature is about 290 mOsm/kg.

26. A composition as defined in claim 24, wherein the polyether is polyether (B) and the pH of the composition is maintained at about 7.4 and the osmolality of the composition at mammalian body temperature is about 290 mOsm/kg.

27. The composition as defined in claim 24, wherein the optional latent form of the counter-ion is present as a microencapsulated component or as an ion-exchange resin, the counter-ion is selected from the group consisting of calcium, strontium, and aluminum, and the ionic polysaccharide is an ammnonium alginate, a metal alginate, or mixtures thereof wherein said counter-ion and said alginate being present at a molar ratio between about 1:1 to about 10:1.

28. The composition as defined in claim 24, wherein the optional latent form of the counter-ion is present as a microencapsulated components or as an ion-exchange resin, the counter-ion is selected from the group consisting of metal phosphates, metaphosphates, pyrophosphates, and tripolyphosphates, and the ionic polysaccharide is chitosan wherein said counter-ion and said chitosan being present at a molar ratio between about 1:1 to about 10:1.

* * * * *

UNITED STATES PATENT AND TRADEMARK OFFICE
CERTIFICATE OF CORRECTION

PATENT NO. : 5,346,703
DATED : September 13, 1994
INVENTOR(S) : Tacey X. Viegas, Lorraine E. Reeve, Raymond L. Henry It is certified that error appears in the above-indentified patent and that said Letters Patent is hereby corrected as shown below:

Col. 14, line 26, the word "antiastrunatics" should be --antiasthmatics--

Col. 16, line 56, the formula: "$HO(C_2H_4O)_b(C_4H_8O)_8(C_2H_4O)_bH$" should be --$HO(C_2H_4O)_b(C_4H_8O)_a(C_2H_4O)_bH$--

Col. 16, line 59, the formula "$(C_4H_8O)_8$" should be --$(C_4H_8O)_a$--

Col. 16, line 67, the formula "$HO(C_2H_4O)_b(C_3H_6O)_8(C_2H_4O)_bH$" should be -- $HO(C_2H_4O)_b(C_3H_6O)_a(C_2H_4O)_bH$--

Col. 17, line 2, the formula "$(C_3H_6O)_8$" should be --$(C_3H_6O)_a$--

Col. 17, line 56, the word "!0%" should be --10%--

Col. 17, line 58, the word "sais" should be --said--

Col. 18, line 54, please delete the word "trichomonocidal,"

Signed and Sealed this

Eighth Day of November, 1994

Attest:

BRUCE LEHMAN

Attesting Officer  Commissioner of Patents and Trademarks